(12) United States Patent
Zumbrum

(10) Patent No.: US 10,799,869 B2
(45) Date of Patent: Oct. 13, 2020

(54) FLUID TRANSPORT APPARATUS, FLEXIBLE CONDUIT, METHOD OF MANUFACTURING FLEXIBLE CONDUIT, AND STORAGE METHOD

(71) Applicant: ALLPURE TECHNOLOGIES, LLC., New Oxford, PA (US)

(72) Inventor: Michael A. Zumbrum, New Oxford, PA (US)

(73) Assignee: Sartorius Stedim North America Inc., Bohemia, NY (US)

( * ) Notice: Subject to any disclaimer, the term of this patent is extended or adjusted under 35 U.S.C. 154(b) by 563 days.

(21) Appl. No.: 15/440,706

(22) Filed: Feb. 23, 2017

(65) Prior Publication Data

US 2018/0238475 A1    Aug. 23, 2018

(51) Int. Cl.
| | | |
|---|---|---|
| *B01L 99/00* | (2010.01) | |
| *B01L 3/00* | (2006.01) | |
| *A01N 1/02* | (2006.01) | |
| *A61M 39/00* | (2006.01) | |
| *A61M 39/08* | (2006.01) | |

(52) U.S. Cl.
CPC ............ *B01L 3/561* (2013.01); *A01N 1/0268* (2013.01); *A61M 39/00* (2013.01); *A61M 39/08* (2013.01); *B01L 2300/123* (2013.01); *B01L 2300/1894* (2013.01)

(58) Field of Classification Search
CPC ............................ B01L 2300/123; B01L 3/561
USPC .......................................... 422/546, 545, 544
See application file for complete search history.

(56) References Cited

U.S. PATENT DOCUMENTS

| | | | |
|---|---|---|---|
| 5,482,446 A | 1/1996 | Williamson et al. | |
| 6,451,396 B1 | 9/2002 | Zumbrum et al. | |
| 6,802,961 B2 | 10/2004 | Jackson | |
| 6,979,362 B2 | 12/2005 | Jackson | |
| 7,219,677 B1 | 5/2007 | Jackson | |
| 7,601,112 B2 | 10/2009 | Jackson | |
| 7,901,540 B2 | 3/2011 | Jackson | |
| 8,197,603 B2 | 6/2012 | Jackson | |
| 8,505,586 B2 | 8/2013 | Zumbrum | |
| 9,376,305 B2 | 6/2016 | Zumbrum | |
| 2007/0216061 A1 | 9/2007 | Karthauser et al. | |
| 2008/0166509 A1* | 7/2008 | Simon ................... | C08L 83/04 428/35.7 |
| 2011/0155274 A1 | 6/2011 | Zumbrum | |
| 2012/0192987 A1* | 8/2012 | Haschke ............... | A61M 39/08 138/137 |
| 2014/0103077 A1 | 4/2014 | Zumbrum | |
| 2014/0190570 A1 | 7/2014 | Zumbrum | |
| 2016/0311673 A1 | 10/2016 | Zumbrum | |
| 2016/0311674 A1 | 10/2016 | Zumbrum | |

FOREIGN PATENT DOCUMENTS

| | | |
|---|---|---|
| WO | 2010008396 | 1/2010 |
| WO | 2012177250 | 12/2012 |
| WO | 2015084388 | 6/2015 |

OTHER PUBLICATIONS

Kinetx CO2 Immersion Cleaning Systems, http://cleanlogix.com/index.php/products/spray-cleaning/spray-cleaning-5, known at least as early as Nov. 2, 2015, 1 pg.
International Standard ISO 10993-18, Biological Evaluation of Medical Devices—Part 18: Chemical Characterization of Materials, Jul. 1, 2005, 24 pgs.
International Search Report for PCT/US2018/018481, dated Apr. 23, 2018, 10 pgs.
Silicones, Bruce Hardman and Arnold Torkelson—General Electric Company, reprinted from Encyclopedia of Polymer Science and Engineering, Copyright 1989, 20 pgs.
EnvironMolds ArtMolds, What is Condensation Cure and Addition Cure Silicone, www.artmolds.com, known at least as early as Feb. 22, 2017, 2 pgs.
TBL Performance Plastics, So, Which is Better, Platinum or Peroxide?, www.tblplastics.com, known at least as early as Feb. 22, 2017, 5 pgs.
Simtec Silicone Parts, Platinum-Cured Silicone: Its Roles and Uses in Today's Custom Manufacturing Processes, www.simtec-silicone.com, known at least as early as Feb. 22, 2017, 5 pgs.

* cited by examiner

*Primary Examiner* — Natalia Levkovich
(74) *Attorney, Agent, or Firm* — Womble Bond Dickinson (US) LLP

(57) ABSTRACT

A fluid transport apparatus defining an aseptic pathway configured to direct fluids therethrough is provided. The fluid transport apparatus may include a conduit extending between a first terminus and a second terminus. The conduit may include platinum catalyzed silicone rubber having methyl and phenyl side groups. The conduit may have a storage modulus of $10^8$ or less Pascals at −75 degrees Celsius. At least one fitting may be connected to the first terminus. A fluid storage accessory may be engaged with the second terminus. A related flexible conduit, method of manufacturing a flexible conduit, and storage method are also provided.

20 Claims, 12 Drawing Sheets

FLUID TRANSPORT APPARATUS, FLEXIBLE CONDUIT, METHOD OF MANUFACTURING FLEXIBLE CONDUIT, AND STORAGE METHOD

TECHNICAL FIELD

This disclosure relates generally to conduits for transporting fluids and associated fluid transport apparatuses and methods.

BACKGROUND

Certain processes such as pharmaceutical development and biological testing may employ vessels and conduits to retain and transport various fluids. During such processes, it may be necessary to freeze the fluids or otherwise expose the fluids to relatively cold temperatures such as those associated with cryogenics. In view of the relatively cold temperatures, the particular vessels and conduits and any accompanying accessories must be carefully selected to tolerate such conditions. In this regard, by way of example, some materials may become brittle and/or crack at low temperatures. By way of further example, other materials may leach contaminants into the fluid that may adversely affect the processes being undertaken.

As such, it may be desirable to provide vessels, conduits, and accompanying accessories with features configured to maintain structural integrity at relatively cold temperatures and configured to not adversely affect a sample retained therein.

SUMMARY

Briefly described, in one aspect there is disclosed a fluid transport apparatus defining an aseptic pathway configured to direct fluids therethrough. The fluid transport apparatus may include a conduit extending between a first terminus and a second terminus. The conduit may include platinum catalyzed silicone rubber having methyl and phenyl side groups. The conduit may have a storage modulus of $10^8$ or less Pascals at −75 degrees Celsius. Further, the fluid transport apparatus may include at least one fitting connected to the first terminus. The fluid transport apparatus may additionally include a fluid storage accessory engaged with the second terminus.

In some embodiments the fluid transport apparatus may have less than 0.5 weight percent extractables. The conduit may have a storage modulus of $10^8$ or less Pascals at −100 degrees Celsius. The conduit may be fluid impervious at −75 degrees Celsius. The conduit may remain fluid impervious at −100 degrees Celsius.

In some embodiments the fluid storage accessory may include a vessel closure. The fluid storage accessory may include a vessel. The fluid transport apparatus may further include a sterilizing vent filter engaged with the vessel configured to allow gaseous transfer therethrough.

In an additional aspect, a flexible conduit for directing fluids therethrough is provided. The flexible conduit may include platinum catalyzed silicone rubber having methyl and phenyl side groups and may have less than 0.5 weight percent extractables. The conduit may have a storage modulus of $10^8$ or less Pascals at −75 degrees Celsius. The flexible conduit may be subjected to supercritical $CO_2$ treatment to render the conduit having less than 0.5 weight percent extractables. The flexible conduit may be further treated with a polar organic co-solvent. There may be substantially none of the polar organic co-solvent in the flexible conduit after treatment.

In an additional aspect, a method of manufacturing a flexible conduit is provided. The method may include extruding and cross-linking a conduit of a desired shape and length. The conduit may include platinum catalyzed silicone rubber having methyl and phenyl side groups. Further, the method may include treating the conduit through the process of supercritical fluid extraction until organic extractables are less than 0.5 weight percent.

In some embodiments the supercritical fluid extraction may be performed using supercritical $CO_2$. The supercritical fluid extraction may be performed using supercritical $CO_2$ and a polar organic co-solvent.

In an additional aspect, a storage method is provided. The method may include providing a biological material. Further, the method may include providing a fluid transport apparatus defining an aseptic pathway configured to direct fluids therethrough. The fluid transport apparatus may include a conduit extending between a first terminus and a second terminus. The conduit may include platinum catalyzed silicone rubber having methyl and phenyl side groups. The conduit may have a storage modulus of $10^8$ or less Pascals at −75 degrees Celsius. The fluid transport apparatus may further include at least one fitting connected to the first terminus. The fluid transport apparatus may additionally include a vessel engaged with the second terminus. The method may further include directing the biological material through the conduit into the vessel. Additionally, the method may include sealing the vessel at the conduit. Further, the method may include cryogenically storing the biological material in the vessel.

In some embodiments providing the biological material may include providing cells. In some embodiments providing the biological material may include providing therapeutic proteins. The method may further include engaging a sterilizing vent filter with the vessel to allow gaseous transfer therethrough.

Thus, a fluid transport apparatus, a flexible conduit, a method of manufacturing a flexible conduit, and a storage method are disclosed that possess distinct attributes and represent distinct improvements over the prior art. These and other aspects, features, and advantages of the fluid transport apparatus, the flexible conduit, the method of manufacturing the flexible conduit, and the storage method of this disclosure will be better understood and appreciated upon review of the detailed description set forth below when taken in conjunction with the accompanying drawing figures, described briefly below. According to common practice, the various features of the drawings may not be drawn to scale. Dimensions and relative sizes of various features and elements in the drawings may be shown enlarged or reduced to illustrate more clearly the embodiments of the present disclosure.

DETAILED DESCRIPTION OF EMBODIMENTS

Certain exemplary embodiments of the present disclosure are described below and illustrated in the accompanying figures. The embodiments described are only for purposes of illustrating the present disclosure and should not be interpreted as limiting the scope of the disclosure, which, of course, is limited only by the claims below. Other embodiments of the disclosure, and certain modifications and improvements of the described embodiments, will occur to those skilled in the art, and all such alternate embodiments, modifications, and improvements are within the scope of the present disclosure.

Figure 1:
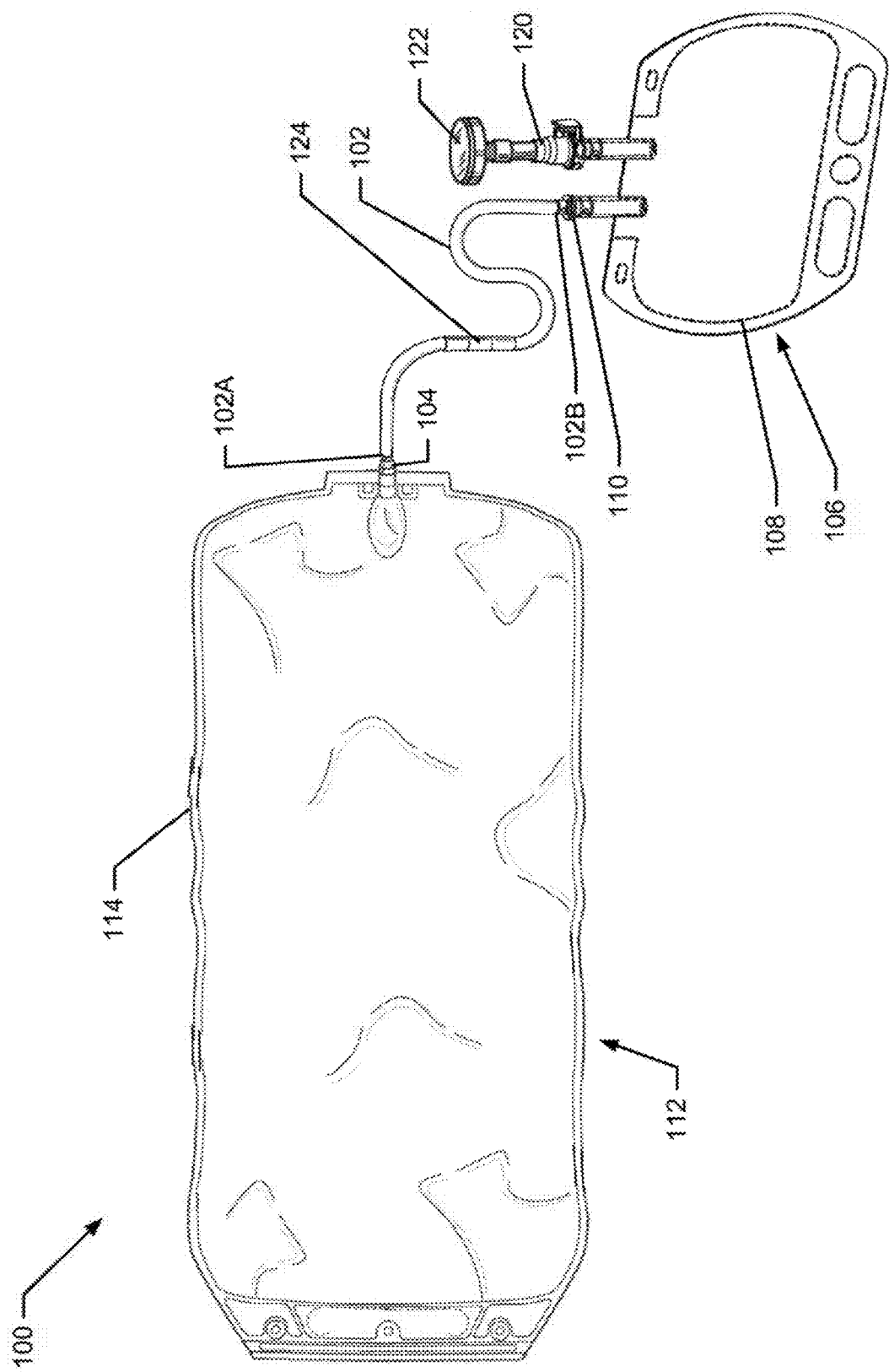
FIG. 1 illustrates a perspective view of a fluid transport apparatus including a conduit. a fluid source, and a vessel according to an example embodiment of the present disclosure.

Referring now in more detail to the drawing figures, wherein like reference numerals indicate like parts throughout the several views, FIG. 1 illustrates a fluid transport apparatus 100 according to an example embodiment of the present disclosure. The fluid transport apparatus 100 may be configured to direct fluids therethrough.

Further, the fluid transport apparatus 100 may be substantially sterile and define an aseptic pathway throughout. In this regard, the fluid transport apparatuses disclosed herein may be assembled and then the entire devices or components thereof may be rendered substantially aseptic by, for example, gamma radiation. Alternatively, the entire devices or components thereof may be rendered substantially aseptic by exposure to steam above 121 degrees Celsius for a period of time long enough to eliminate microorganisms. The entire devices or components thereof may also be rendered aseptic by chemical treatment, such as with ethylene oxide (ETO).

Once rendered substantially aseptic, the fluid transport apparatus may be packaged in an outer container, which may also be rendered substantially aseptic as described above, to maintain the substantially aseptic state until use.

As illustrated, the fluid transport apparatus 100 may include a conduit 102. The conduit 102 may comprise a flexible material, and hence may also be referred to as a flexible conduit. Traditionally, such a conduit 102 may comprise thermoplastic tubing, thermoset tubing, elastomeric tubing, or any combination thereof. Example thermoset materials include silicones, polyurethanes, fluoroelastomers or perfluoropolyethers. Example thermoplastics include C-FLEX, block copolymers of styrene-ethylene-butylene-styrene, PureWeld, PVC, polyolefins, or polyethylene.

However, as described hereinafter, in a preferred embodiment the conduit 102 may comprise platinum catalyzed silicone rubber having methyl and phenyl side groups or phenyl methyl siloxane copolymerized with dimethyl siloxane. In addition to the silicone polymer, the material may include a reinforcing filler such as fused silica, as will preferably be cross-linked to be elastomeric. As discussed hereinafter, the material composition of the conduit 102 may provide certain benefits as compared to existing embodiments of conduits, particularly at low temperatures.

The conduit 102 may extend between a first terminus 102A and a second terminus 102B. At least one fitting 104 may be connected to the first terminus 102A. Further, a fluid storage accessory may be engaged with the second terminus 102B. A variety of fluid storage accessories that may be engaged with the second terminus 102B are described hereinafter.

For example, the fluid storage accessory may comprise a vessel 106. In the illustrated embodiment the vessel 106 comprises a bag (e.g., a bioreactor bag or a sample bag). However, the vessel 106 may additionally comprise, without limitation, an Erlenmeyer flask, a bottle, a syringe, a container, a beaker, a receptacle, a tank, a vat, a vial, a tube (e.g., a centrifuge tube), and the like that are generally used to contain fluids, slurries, and other similar substances. The vessel 106 may be formed from one or more of various materials including, by way of example, polycarbonate (PC), polyethylene terephthalate (PET), polyethylene (PE), polypropylene (PP), polyolefin (PO), polyethersulfone (PES), perfluoroalkoxy (PFA), polytetrafluoroethylene (PTFE), and polyvinylidene fluoride (PVDF).

The vessel 106 may define a cavity 108. The vessel 106 may be configured to retain a fluid (and optionally other materials), which may include a biological material, in the cavity 108. The vessel 106 may receive the fluid from the conduit 102. In this regard, the vessel 106 may include a fitting 110 configured to engage the second terminus 102B of the conduit 102.

Further, the conduit 102 may receive the fluid from a fluid source 112. In the illustrated embodiment the fluid source 112 includes a source vessel 114. In some embodiments, as illustrated, the first terminus 102A of the conduit 102 may directly couple to the source vessel 114 via a fitting 104 (e.g., a barbed fitting). Alternatively, in other embodiments the conduit may receive fluid from the source vessel via an intermediate device. In one example embodiment the intermediate device may comprise a fluid transfer device such as the TAKEONE® aseptic sampling device available from ALLPURE® of New Oxford, Pa.

In some embodiments the vessel 106 may further include a second fitting 120. The second fitting 120 may be configured to engage a vessel accessory. For example, in the illustrated embodiment the second fitting 120 comprises a standard quick connect fitting. Further, in the illustrated embodiment a sterilizing vent filter 122 is engaged with the second fitting 120 of the vessel 106. The sterilizing vent filter 122 may be configured to allow gaseous transfer therethrough such that air may travel into and/or out of the vessel 106. In some embodiments the sterilizing vent filter 122 may define apertures having a size from about 0.1 micron to about 0.3 microns, and preferably about 0.2 microns in order to prevent contaminants from entering the vessel cavity 108 defined by the vessel 106.

Additionally, in some embodiments the conduit 102 may include a sealing device 124. The sealing device 124 may be cut to define an aseptic seal. Thereby, the fluid received in the vessel 106 may be sealed therein by the sealing device 124, which may prevent the fluid from flowing therepast.

In the embodiment described above, the second terminus 102B of the conduit is engaged with the vessel 106. However, as noted above, the second terminus 102B may engage differing fluid storage accessories in other embodiments.

Figure 2:
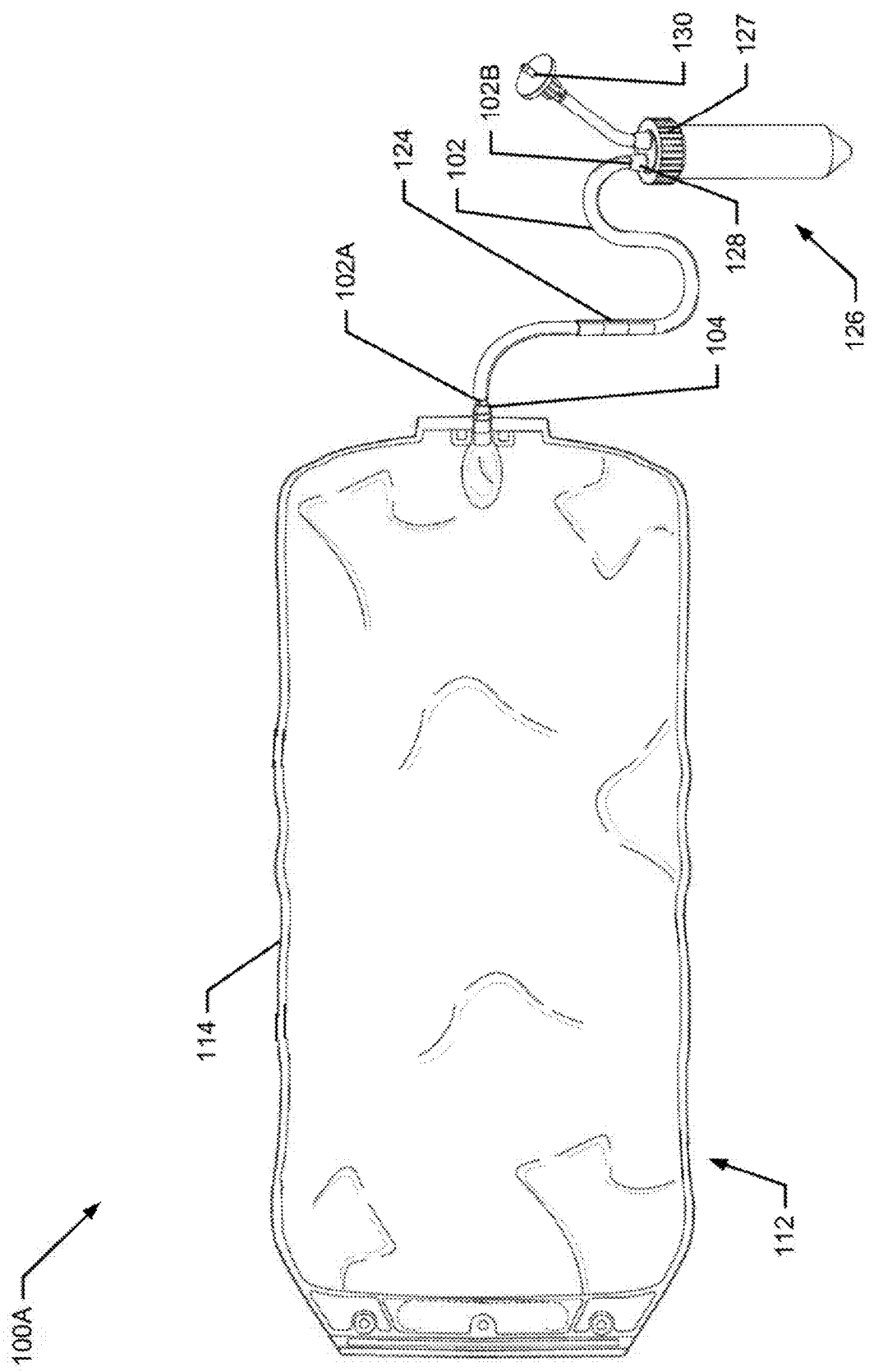
FIG. 2 illustrates a perspective view of a fluid transport apparatus including a conduit, a fluid source, and a centrifuge tube according to an example embodiment of the present disclosure.

For example, FIG. 2 illustrates an alternate embodiment of the fluid transport apparatus 100A. The fluid transport apparatus 100A may be substantially similar to the fluid transport apparatus 100 of FIG. 1 except for the differences noted hereinafter. In particular, the fluid storage accessory comprises a centrifuge tube 126 in the embodiment illustrated in FIG. 2. As illustrated, in some embodiments the fluid storage accessory may further comprise a vessel closure 127 engaged with the centrifuge tube 126. In the illustrated embodiment of the vessel closure 127, the vessel closure is a cap. Suitable caps for the vessel closure 127 include those commonly used in the field of pharmaceutical, biopharmaceutical, and biotechnology processing. The vessel closure 127 may engage the centrifuge tube 126, by way of example, via a threaded connection. Various other connection mechanisms may be employed in other embodiments. By way of example, in other embodiments the connection mechanism may comprise a clamp connection, a welded connection, a bonded connection, or any other mechanical means.

The vessel closure 127 may be made from thermoplastics such as polyolefins, polypropylene, polyethylene, polysulfone, polyester, polycarbonate, and glass filled thermoplastics. The vessel closure 127, however, is not limited to any particular material(s). The vessel closure 127 may also be made from thermosets such as epoxies, pheonolics, and novolacs. The vessel closure 127 may also be a hygienic or sanitary clamp having dimensions disclosed in ASME BPE table DT-5-2 ("Hygienic Clamp Ferrule Standard Dimensions and Tolerances") (2009), which is incorporated by reference herein in its entirety. The vessel closure is not limited to caps or hygienic clamps but may constitute any suitable closure that seals the interior of a vessel from the exterior environment.

The vessel closure 127 may include a fitting 128 configured to engage the second terminus 102B of the conduit 102. As may be understood, the vessel closure 127 may include a second fitting 130 (e.g., a barbed fitting) or additional fittings that may be coupled to a vessel accessory such as the sterilizing vent filter 122 described above with respect to FIG. 1.

Figure 3:
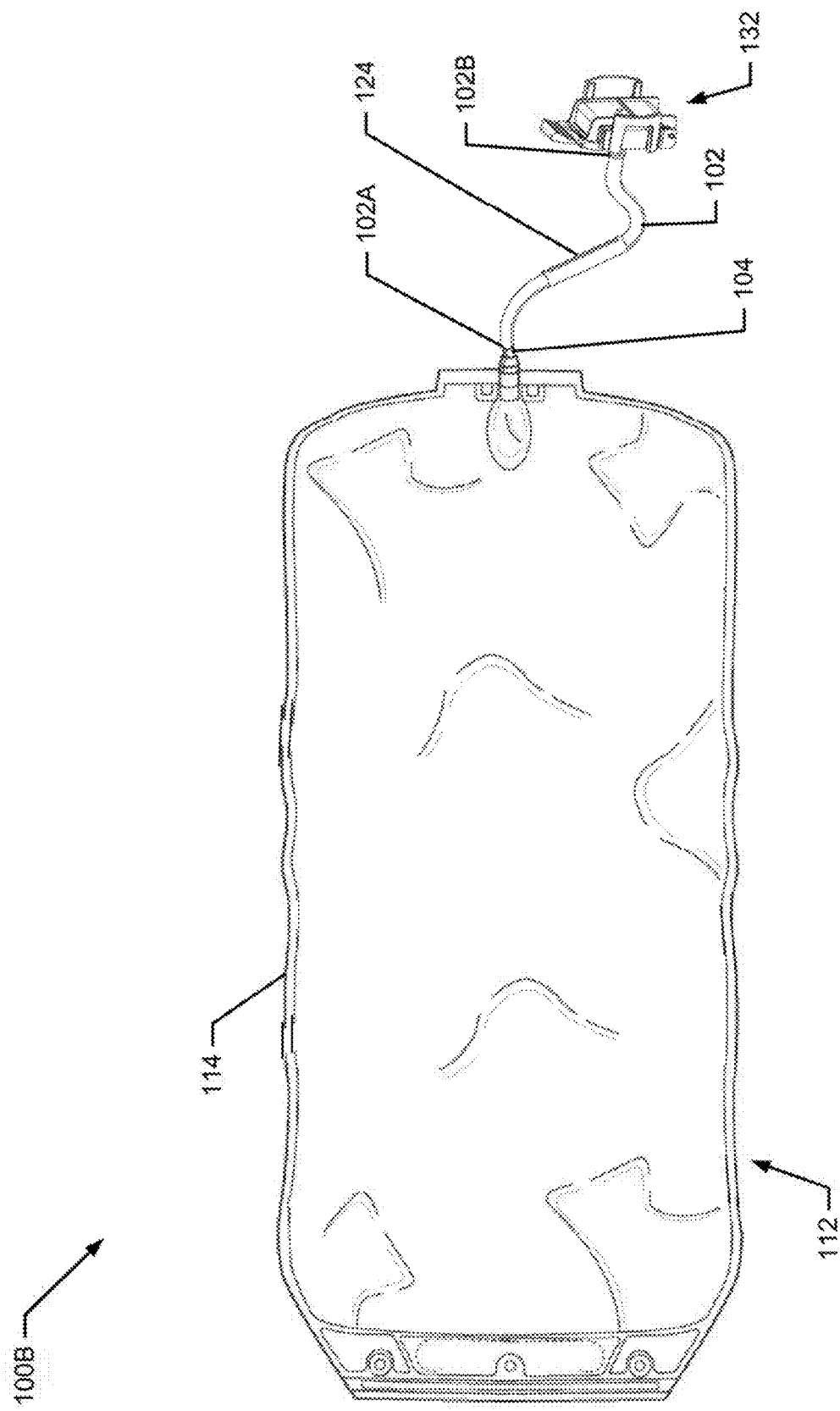
FIG. 3 illustrates a perspective view of a fluid transport apparatus including a conduit, a fluid source, and a connector according to an example embodiment of the present disclosure.

FIG. 3 illustrates an additional alternate embodiment of the fluid transport apparatus 100B that is substantially similar to the fluid transport apparatus 100 of FIG. 1 except for the differences noted hereinafter. In particular, the fluid storage accessory comprises a connector 132. More particularly, in the illustrated example embodiment the connector 132 comprises an ASEPTIQUIK® connector available from Colder Products Company of St. Paul, Minn.

As may be understood, the conduits of the present disclosure may be configured to couple various other devices and apparatuses. Description of the details of the components of the fluid transport apparatuses provided hereinafter may substantially correspond to similarly-named components described above and will not be repeated for brevity purposes.

Figure 4:
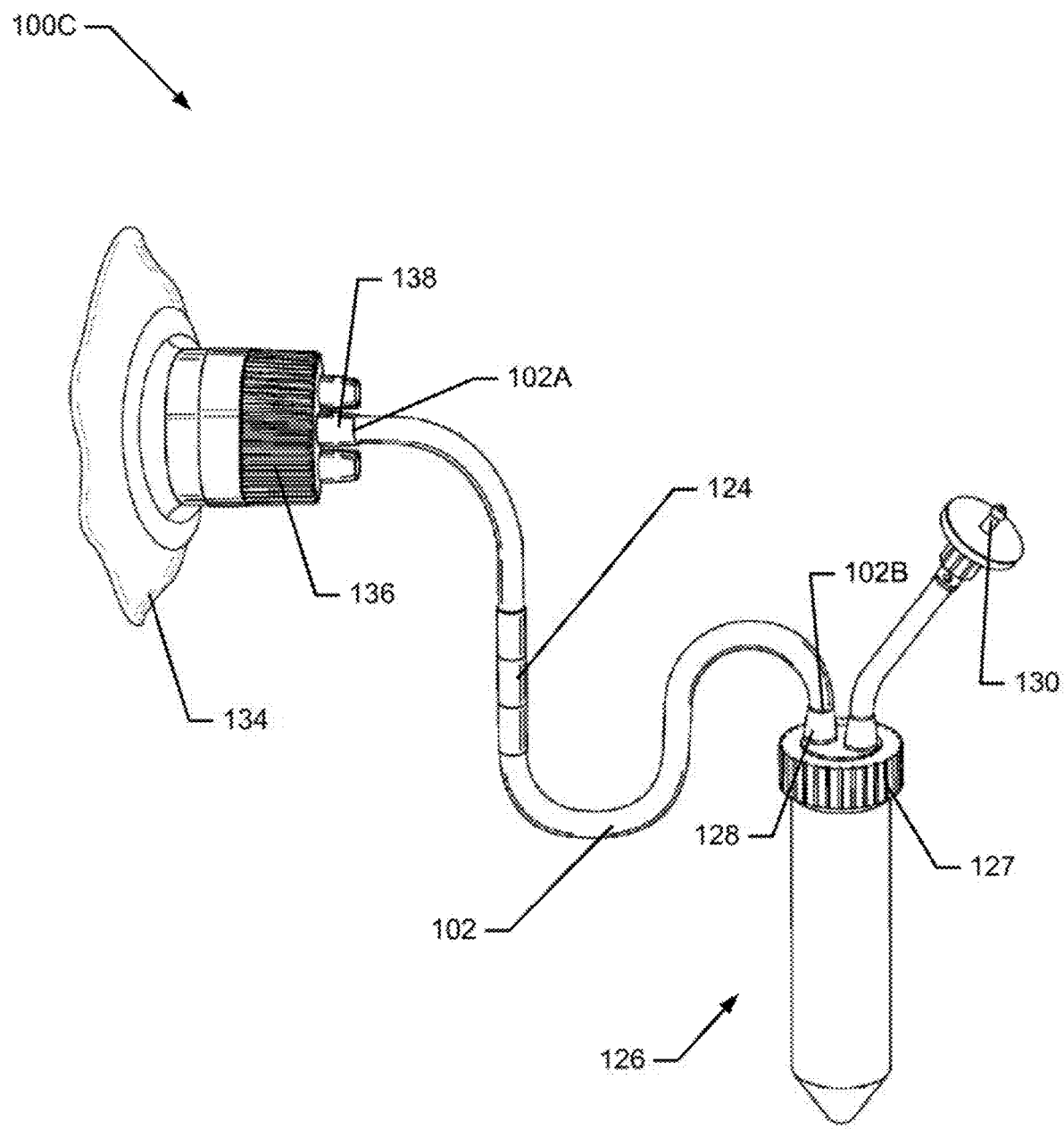
FIG. 4 illustrates a perspective view of a fluid transport apparatus including a conduit, a vessel, a vessel closure, and a centrifuge tube according to an example embodiment of the present disclosure.

By way of example, FIG. 4 illustrates an embodiment of the fluid transport apparatus 100D wherein the conduit 102 is coupled at the second terminus 102B to the centrifuge tube 126 via the vessel closure 127, similar to the configuration illustrated in FIG. 2. Further, the first terminus 102A of the conduit 102 is engaged with a vessel 134 via a vessel closure 136, which may include a fitting 138.

Figure 5:
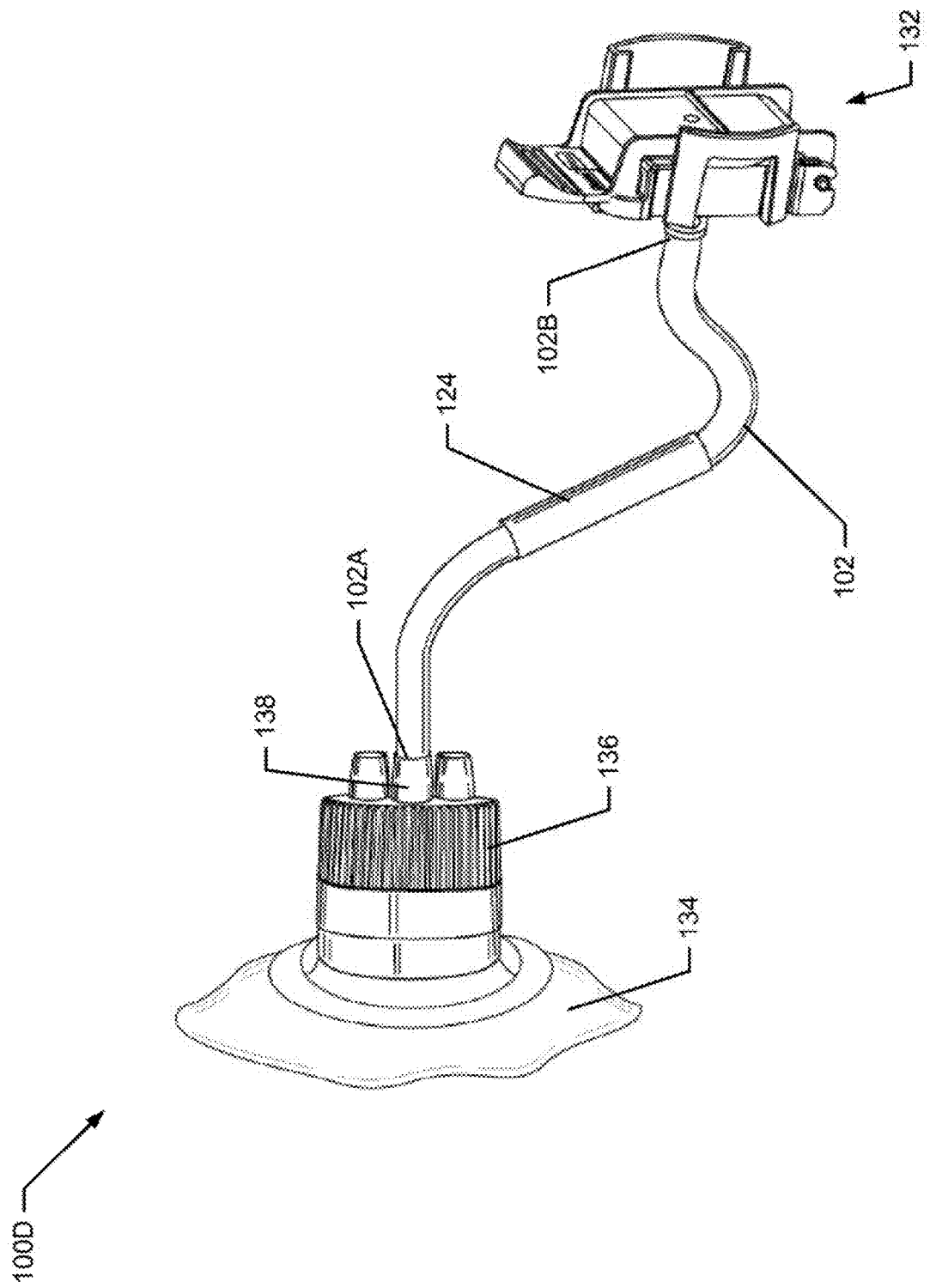
FIG. 5 illustrates a perspective view of a fluid transport apparatus including a conduit, a vessel, a vessel closure, and a connector according to an example embodiment of the present disclosure.

FIG. 5 illustrates an embodiment of the fluid transport apparatus 100D wherein the first terminus 102A of the conduit 102 is engaged with the vessel 134 via the vessel closure 136, which may include the fitting 138. Further, the second terminus 102B of the conduit 102 is engaged with the connector 132, which may comprise an ASEPTIQUIK® connector available from Colder Products Company of St. Paul, Minn.

Figure 6:
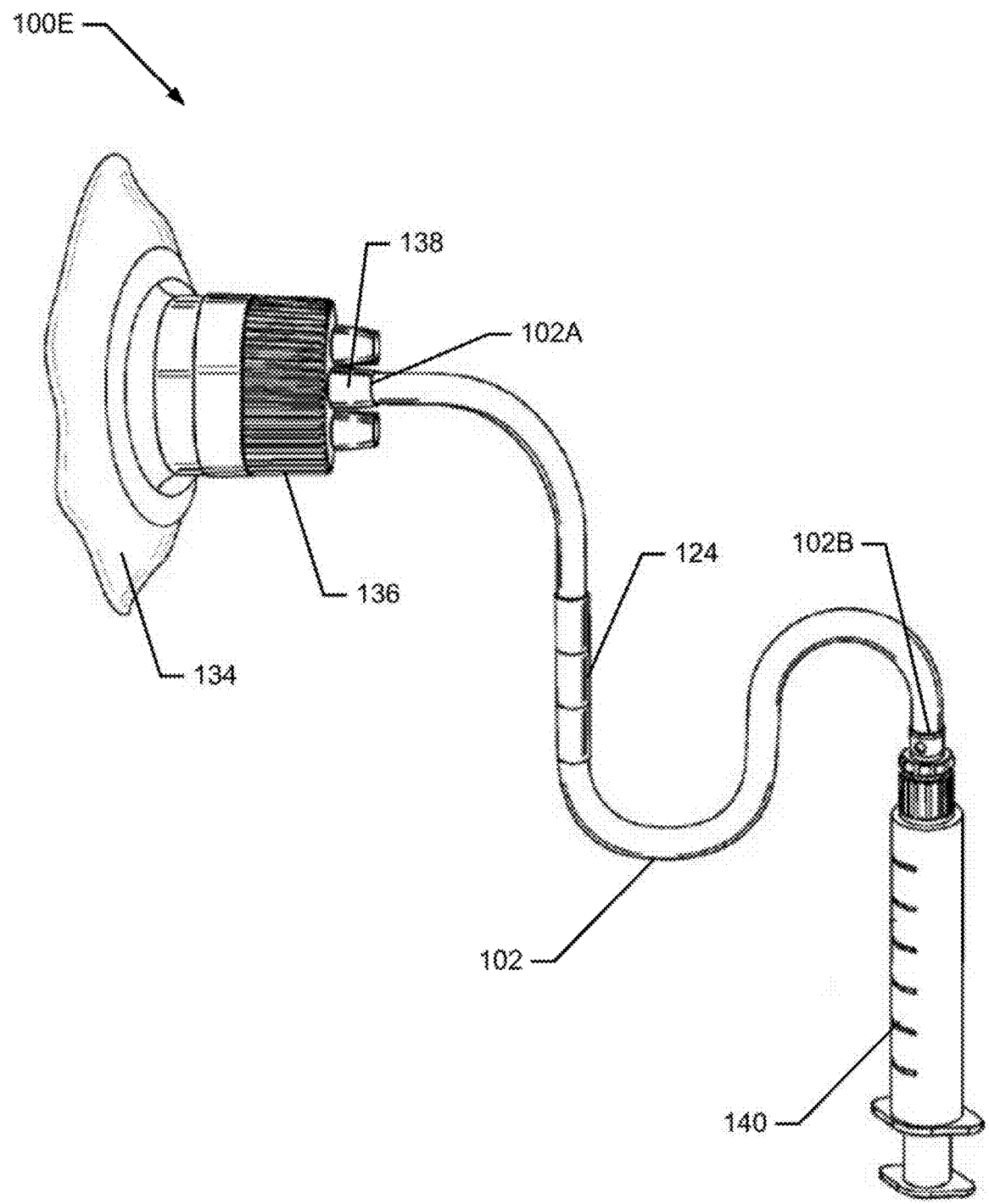
FIG. 6 illustrates a perspective view of a fluid transport apparatus including a conduit, a vessel, a vessel closure, and a syringe according to an example embodiment of the present disclosure.

FIG. 6 illustrates an embodiment of the fluid transport apparatus 100E wherein the first terminus 102A of the conduit 102 is engaged with the vessel 134 via the vessel closure 136, which may include the fitting 138. Further, the second terminus 102B of the conduit 102 is engaged with a syringe 140.

Figure 7:
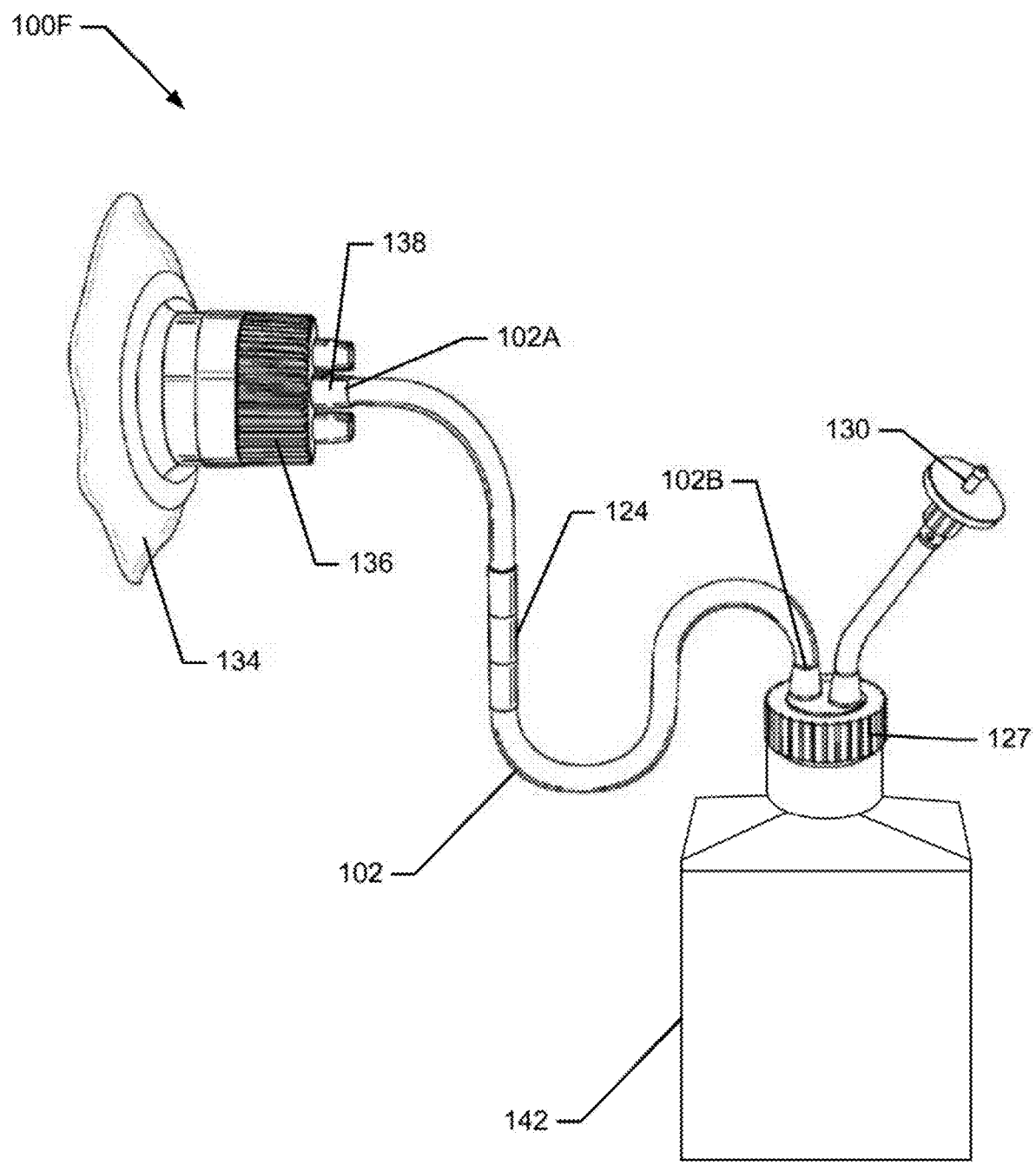
FIG. 7 illustrates a perspective view of a fluid transport apparatus including a conduit, a vessel, a vessel closure, and a bottle according to an example embodiment of the present disclosure.

FIG. 7 illustrates an embodiment of the fluid transport apparatus 100F wherein the first terminus 102A of the conduit 102 is engaged with the vessel 134 via the vessel closure 136, which may include the fitting 138. Further, the second terminus 102B of the conduit 102 is engaged with a bottle 142 (e.g., a square polyethylene terephthalate copolyester (PETG) bottle) via the vessel closure 127, similar to the configuration illustrated in FIG. 2.

Figure 8:
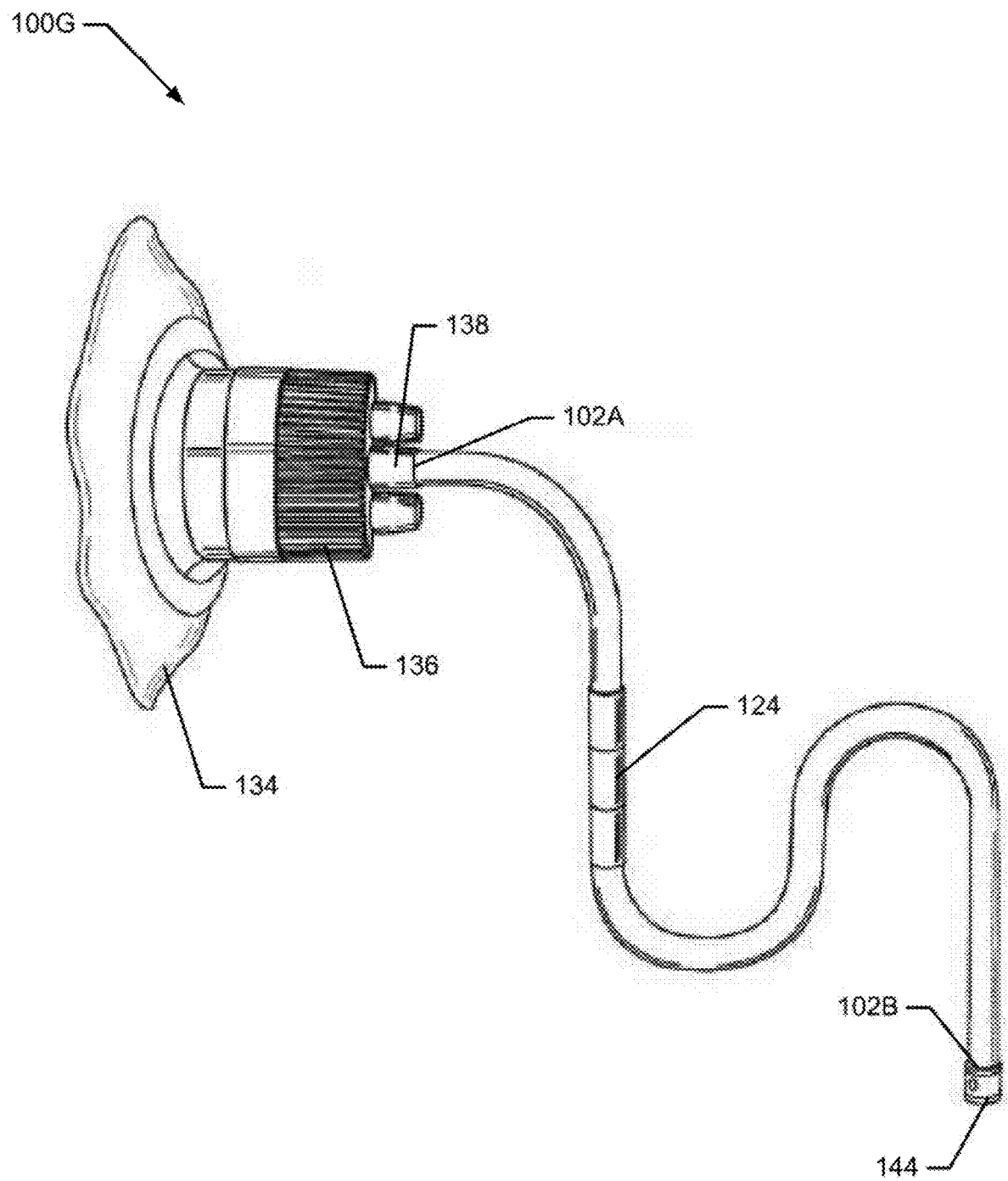
FIG. 8 illustrates a perspective view of a fluid transport apparatus including a conduit, a vessel, a vessel closure, and a plug according to an example embodiment of the present disclosure.

FIG. 8 illustrates an embodiment of the fluid transport apparatus 100G wherein the first terminus 102A of the conduit 102 is engaged with the vessel 134 via the vessel closure 136, which may include the fitting 138. Further, the second terminus 102B of the conduit 102 is engaged with a plug 144, which may be removed for connection to another device or to allow fluid transfer therethrough.

Figure 9:
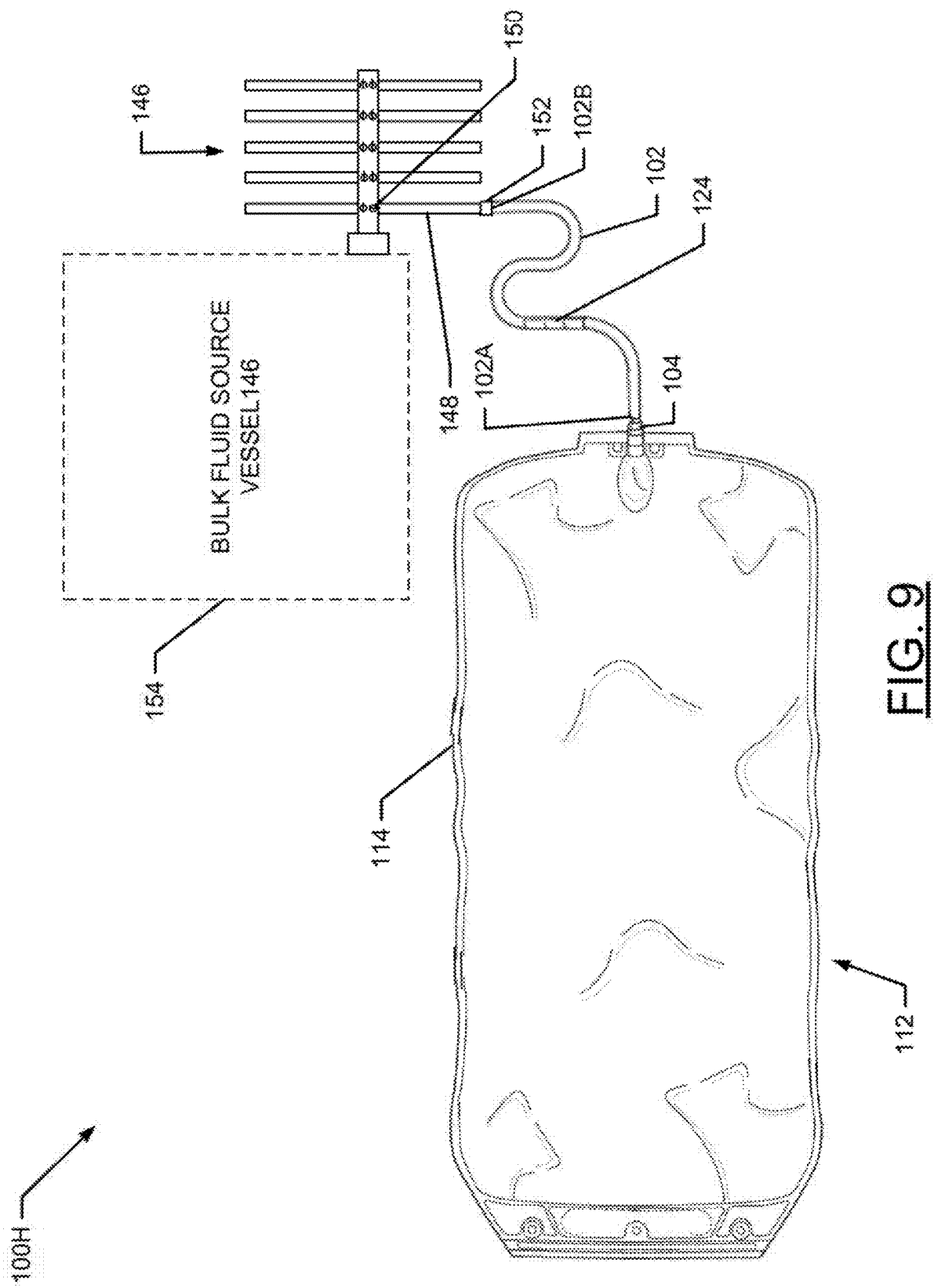
FIG. 9 illustrates a perspective view of a fluid transport apparatus including a conduit, a bulk fluid source vessel, a manifold, and a recipient vessel according to an example embodiment of the present disclosure.

FIG. 9 illustrates an embodiment of the fluid transport apparatus 100H wherein the first terminus 102A of the conduit 102 is engaged with a recipient vessel, which may be the same as the source vessel 112 described above with respect to FIG. 1. Further, the second terminus 102B is engaged with a manifold 146. The manifold 146 may include a plurality of conduits 148, which may be imbedded in a body thereof. Further, the manifold may include a plurality of valves 150, which may control flow of fluid through the conduits 148. The second terminus 102B may be engaged with one of the conduits 148 of the manifold 146 via a connector 152 (e.g., a barbed connector). The manifold 146 may be coupled to a bulk fluid source vessel 154, which may be configured to contain a relatively large quantity of fluid (e.g., from about 300 liters to about 500 liters). Thereby, fluid retained in the bulk reservoir 154 may be directed through the manifold 146 to the recipient vessel 112. An example bulk fluid source vessel 154, which is schematically illustrated in FIG. 9, is sold under the name PALLENTANK® by Sartorius of Göttingen, Germany.

Thus, as described above, various configurations of the fluid transport apparatus may be employed. Regardless of the particular configuration of the devices engaged therewith, the conduit 102 and the other conduits described herein, including the conduits 148 included in the manifold 146, may be formed from material configured to be flexible and fluid impervious in a relatively wide range of temperatures. In this regard, the normal lab, manufacturing and processing temperatures are unlikely to substantially exceed 121 degrees Celsius at an upper end, at which sterilization thereof may occur. Further, storage and treatment of biological samples may involve cooling the biological samples to temperatures down to about −100 degrees Celsius. As such, it may be desirable to form the conduit 102 from a material configured to withstand temperatures within this range.

Traditionally, materials such as thermoplastic elastomer and silicone have been employed to form conduits used in labs and other processing facilities. While such materials may be suitable for usage at ordinary room temperature (e.g., about 20 degrees Celsius), they may not be suitable for usage in relatively cold conditions such as down to about −100 degrees Celsius. In this regard, such traditional materials employed in conduits become brittle at low temperatures. Thereby, such traditional materials may crack when the conduit is moved, which may result in a fluid leak and/or contamination.

Accordingly, conduits comprising such traditional materials are generally not exposed to the cold conditions noted above. Rather, for example, after a fluid sample is directed through a conduit into a vessel, the conduit is removed from the vessel and the vessel is sealed prior to subjecting the vessel to the cold temperatures. Removal of the conduit involves an additional step and presents the possibility for contamination to occur. Alternatively, the conduit may be formed from a material that is rigid at ordinary lab conditions (e.g., 20 degrees Celsius) and that is configured to withstand such low temperatures (e.g., polytetrafluoroethylene). However, usage of rigid conduit may be inconvenient for receiving fluid flow thereto due to the requirement for precise component alignment to form the necessary connections.

However, by forming the conduit from a material that is flexible at ordinary room temperature, and that is configured to remain flexible at the low temperatures, and thereby avoid cracking, the conduit may remain fluid impervious. Accordingly, by forming the conduit 102 from a material configured to remain flexible at the relatively cold temperatures discussed herein, the conduit may remain in engagement with a vessel, a vessel closure, or any other device coupled thereto, and the entire assembly may be exposed to the cold temperatures. In this embodiment, in order to seal the fluid in the assembly, the vessel closure may be clipped. Thereby, the assembly may remain aseptic.

Thus, the conduit 102 may comprise a material configured to remain flexible across a wide range of temperatures. In this regard, as noted above, the conduit 102 may comprise platinum catalyzed silicone rubber having methyl and phenyl side groups. Such a material does not crystallize at the relatively cold temperatures discussed herein and hence avoids becoming brittle and cracking. In this regard, whereas methyl silicone crystallizes at about −50 degrees Celsius, the phenyl side group included in the preferred material according to the present disclosure may prevent or delay the crystallization to a lower temperature.

Polymers composed of long molecular chains have unique viscoelastic properties, which combine the characteristics of elastic solids and Newtonian fluids. These properties are quantified by a storage modulus and a loss modulus. The storage modulus measures the stored energy, representing the elastic portion of a polymer material. The loss modulus measures the energy dissipated as heat, representing the viscous portion of the polymer material.

Figure 10:
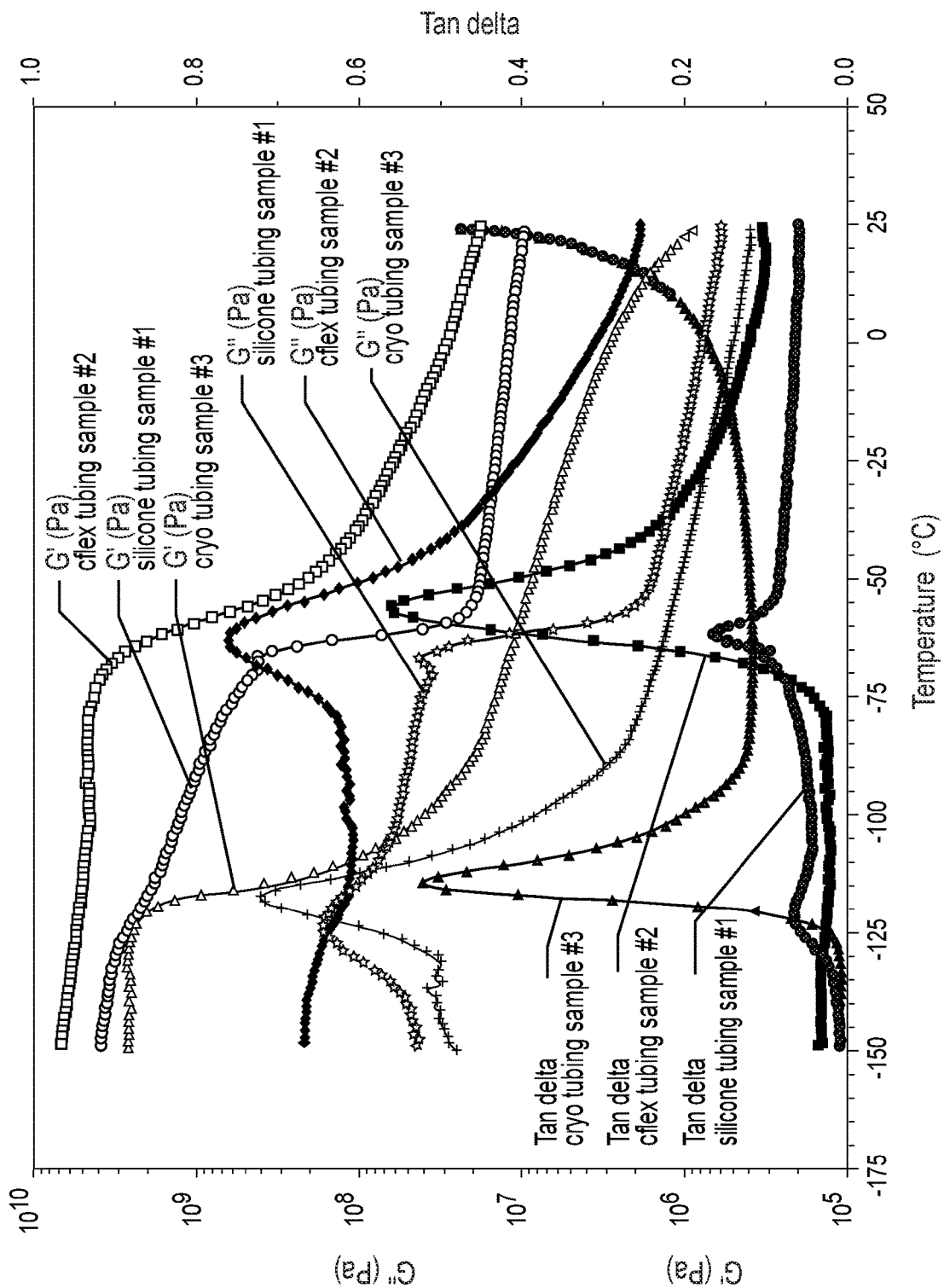
FIG. 10 illustrates loss and storage moduli of various materials in Pascals on the left vertical axis versus temperature in degrees Celsius on the horizontal axis.

In this regard, FIG. 10 illustrates loss and storage moduli of various materials in Pascals on the left vertical axis versus temperature in degrees Celsius on the horizontal axis. In particular, with reference to the left-most starting points of the curves illustrated in the graph, the three lines at the top of the graph illustrate the storage modulus versus temperature and the three middle lines illustrate the loss modulus versus temperature. The three bottom lines illustrate the noted loss tangent, which is a ratio of the loss modulus (E″) to the storage modulus (E′).

The curves in the graph illustrated in FIG. 10 each include triangles, squares, or circles. The triangles correspond to platinum catalyzed silicone rubber having methyl and phenyl side groups, which is a preferred material according to an example embodiment of the present disclosure. The lines including squares correspond to C-FLEX material, a thermoplastic elastomer tubing, available from Saint-Gobain of Charny, France. The lines including circles correspond to standard silicone material (e.g., dimethyl silicone).

A lesser storage modulus corresponds to greater flexibility. A storage modulus of $10^8$ or less Pascals may be desirable in that it may provide sufficient flexibility to avoid cracking of the conduit 102. As illustrated in FIG. 10, the platinum catalyzed silicone rubber having methyl and phenyl side groups defines a storage modulus of $10^8$ or less Pascals down to a temperature of about −108 degrees Celsius. In contrast, the standard silicone material defines a storage modulus of $10^8$ or less Pascals down to a temperature of only about −63 degrees Celsius and the C-FLEX material defines a storage modulus of $10^8$ or less Pascals down to a temperature of only about −38 degrees Celsius. Accordingly, the standard silicone material may define greater flexibility at relatively low temperatures than the C-FLEX material, and the platinum catalyzed silicone rubber having methyl and phenyl side groups may define a greater flexibility at relatively low temperatures than both the standard silicone material and the C-FLEX material.

In view of the platinum catalyzed silicone rubber having methyl and phenyl side groups defining a storage modulus of less than $10^8$ or less Pascals down to about −108 degrees Celsius, this material may remain resistant to cracking, and hence fluid impervious, at such low temperatures. In contrast, as a result of the other materials becoming relatively less elastic (i.e., more brittle), the C-FLEX and the silicone material may be more prone to cracking at relatively warmer temperatures. Thus, whereas the platinum catalyzed silicone rubber having methyl and phenyl side groups may remain fluid impervious in normal lab conditions (e.g., from about 130 degrees Celsius to about −100 degrees Celsius), the silicone rubber and C-Flex material may become brittle and crack at relatively cold temperatures.

Further, in some embodiments the platinum catalyzed silicone rubber having methyl and phenyl side groups may have less than 0.5 weight percent extractables. Extractables, as used herein, refers to compounds removable by a solvent such as toluene under exhaustive conditions. Soxhlet extractors are typically used to remove extractables as their total weight can be determined gravimetrically or chromatographically. Example extractables that may be removed from the platinum catalyzed silicone rubber having methyl and phenyl side groups include cyclic oligomers of siloxane and low molecular weight siloxanes.

Removal of extractables may avoid issues with respect to contamination of the samples received in the conduit 102 (see, FIGS. 1-8), which may skew results during testing, affect the efficacy of a pharmaceutical product or other product produced therein, or cause other problems. In this regard, usage of platinum catalyzed silicone rubber having methyl and phenyl side groups in conduits and other such fluid processing components contacting fluids has generally been avoided because of concerns with respect to chemical leaching into the samples. However, by removing the extractables in the manner described herein, such concerns may be alleviated.

The conduit 102 may be formed by an extrusion process. Thereafter, the conduit 102 may be subjected to an extractables removal process. The particular process employed to remove the extractables may vary. In some embodiments the conduit 102 may be subjected to supercritical $CO_2$ treatment to render the conduit having less than 0.5 weight percent extractables. For example, the conduit 102 may be treated in a KinetX $CO_2$ immersion cleaning system, available from Clean Logix LLC of Valencia, Calif. In some embodiments the supercritical $CO_2$ treatment may occur at about 20 degrees Celsius at about 4 ATM. This process may solubilize dissolvable substances to remove the extractables from the material forming the conduit 102. Usage of supercritical $CO_2$ treatment, rather than solvent extraction, may avoid issues with respect to any residual solvent remaining on the conduit 102.

However, in some embodiments, the conduit 102 may be additionally or alternatively treated with a polar organic co-solvent to render the conduit having less than 0.5 weight percent extractables. In some embodiments substantially none of the polar organic co-solvent remains in the flexible conduit after treatment. Thereby, issues with respect to contamination from the polar organic co-solvent may also be avoided.

Testing of the material forming the conduit 102 for such extractables may be conducted in accordance with International Standard ISO 10993-18:2005(E), which is incorporated herein by references. Further, as a result of employing the extractable removal described herein, biological samples directed through the conduit 102 may comply with the International Conference of Harmonization Harmonized Tripartite Guideline regarding Impurities in New Drug Substances Q3A(R2), dated Oct. 25, 2006, which is incorporated herein by reference.

In the embodiments provided above, the conduit 102 is generally described as being included in a fluid transport apparatus. However, as may be understood, the conduit 102 may be employed alone or in combination with other apparatuses or systems.

Figure 11:
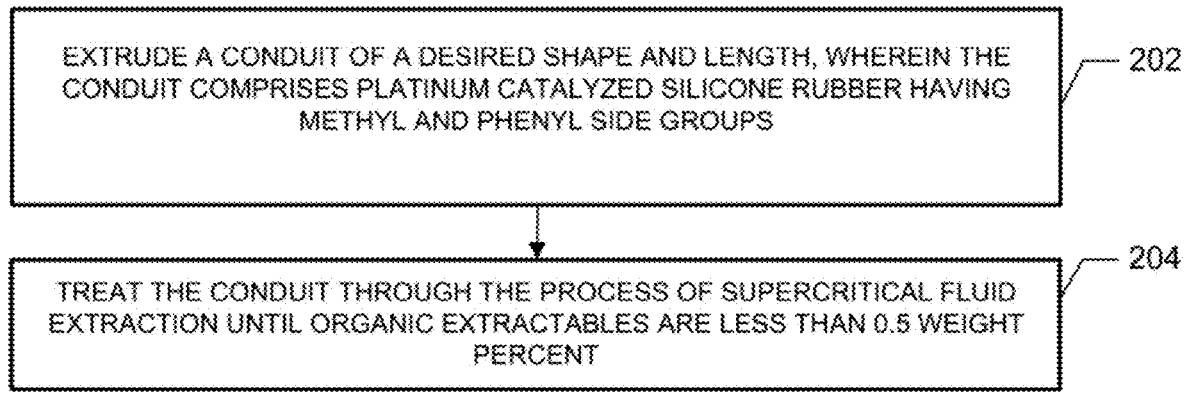
FIG. 11 schematically illustrates a method of manufacturing a flexible conduit according to an example embodiment of the present disclosure.

In an additional embodiment, a method of manufacturing a flexible conduit is provided. As illustrated in FIG. 11, the method may include extruding a conduit of a desired shape and length, wherein the conduit comprises platinum catalyzed silicone rubber having methyl and phenyl side groups at operation 202. Further, the method may include treating the conduit through the process of supercritical fluid extraction until organic extractables are less than 0.5 weight percent at operation 204.

In some embodiments the supercritical fluid extraction at operation 204 is performed using supercritical $CO_2$. The supercritical fluid extraction at operation 204 may be performed using supercritical $CO_2$ and a polar organic co-solvent.

Figure 12:
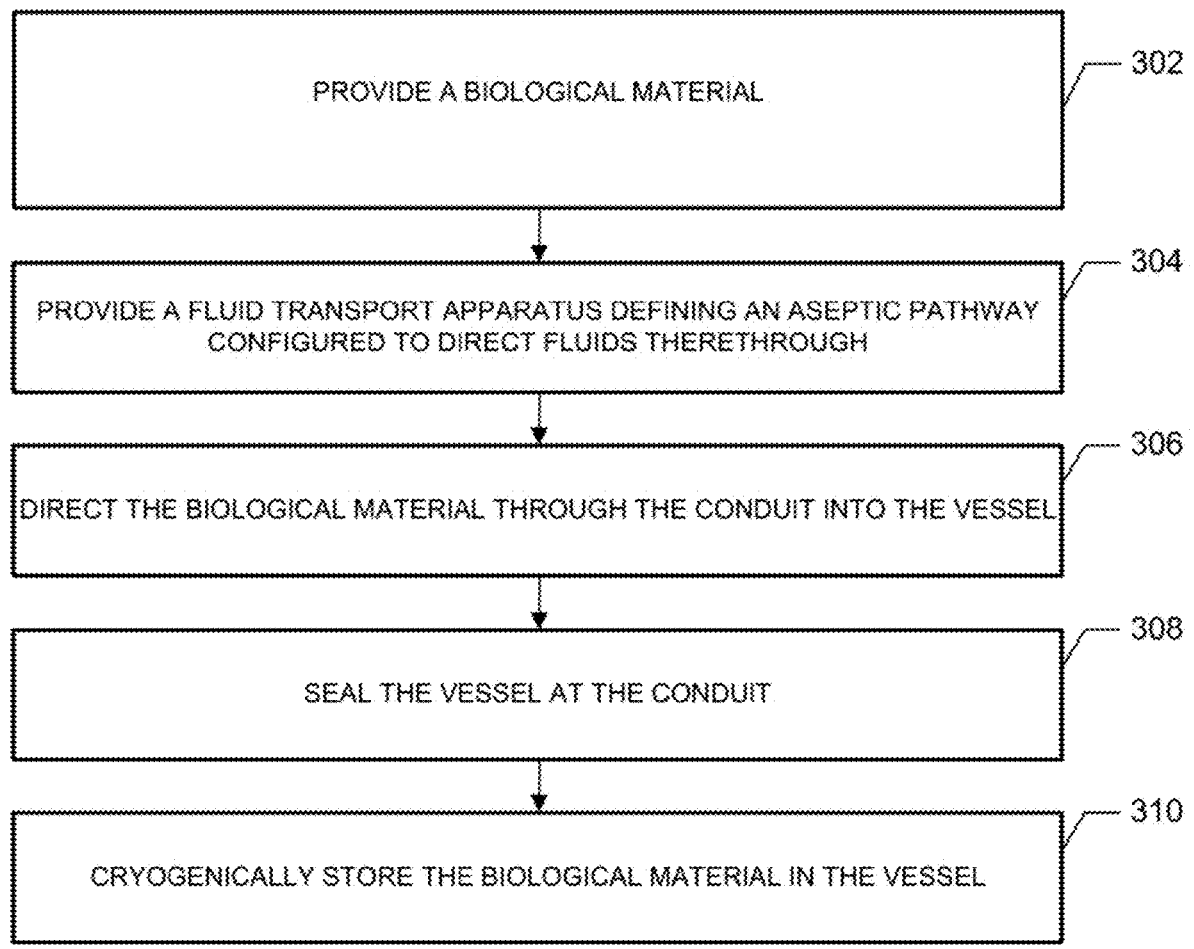
FIG. 12 schematically illustrates a storage method according to an example embodiment of the present disclosure.

In a further embodiment, a storage method is provided. As illustrated in FIG. 12, the method may include providing a biological material at operation 302. Further, the method may include providing a fluid transport apparatus defining an aseptic pathway configured to direct fluids therethrough at operation 304. The fluid transport apparatus may comprise a conduit extending between a first terminus and a second terminus. The conduit may include platinum catalyzed silicone rubber having methyl and phenyl side groups. The conduit may have a storage modulus of $10^8$ or less Pascals at −75 degrees Celsius. Further, the fluid transport apparatus may include at least one fitting connected to the first terminus and a vessel engaged with the second terminus.

The method may additionally include directing the biological material through the conduit into the vessel at operation 306. Further, the method may include sealing the vessel at the conduit at operation 308. Additionally, the method may include cryogenically storing the biological material in the vessel at operation 310.

In some embodiments providing the biological material at operation 302 may include providing cells. In another embodiment providing the biological material at operation 302 may include providing therapeutic proteins. The method may additionally include engaging a sterilizing vent filter with the vessel to allow gaseous transfer therethrough.

The foregoing descriptions of fluid transport apparatuses, conduits, methods of manufacturing flexible conduits, and storage methods illustrate and describe various embodiments. As various changes can be made in the above embodiments without departing from the scope of the present disclosure recited and claimed herein, it is intended that all matter contained in the above description or shown in the accompanying figures shall be interpreted as illustrative and not limiting. Furthermore, the scope of the present disclosure covers various modifications, combinations, alterations, etc., of the above-described embodiments that all are within the scope of the claims. Additionally, the disclosure shows and describes only selected embodiments of the present disclosure, but the present disclosure is capable of use in various other combinations, modifications, and environments and is capable of changes or modifications within the scope of the disclosure as expressed herein, commensurate with the above teachings, and/or within the skill or knowledge of artisans in the relevant art. Furthermore, certain features and characteristics of each embodiment may be selectively interchanged and applied to other illustrated and non-illustrated embodiments of the present disclosure without departing from the scope of the present disclosure.

The invention claimed is:

1. A fluid transport apparatus defining an aseptic pathway configured to direct fluids therethrough, the fluid transport apparatus comprising:
    a conduit having a first terminus and a second terminus, the conduit extending between the first terminus and the second terminus, the conduit formed of platinum catalyzed silicone rubber having methyl and phenyl side groups, the conduit having a storage modulus of $10^8$ or less Pascals at −75 degrees Celsius;
    at least one fitting connected to the first terminus; and
    a fluid storage accessory engaged with the second terminus.

2. The fluid transport apparatus of claim 1, wherein the platinum catalyzed silicone rubber having methyl and phenyl side groups has less than 0.5 weight percent extractables.

3. The fluid transport apparatus of claim 1, wherein the conduit has a storage modulus of $10^8$ or less Pascals at −100 degrees Celsius.

4. The fluid transport apparatus of claim 1, wherein the conduit is fluid impervious at −75 degrees Celsius.

5. The fluid transport apparatus of claim 4, wherein the conduit remains fluid impervious at −100 degrees Celsius.

6. The fluid transport apparatus of claim 1, wherein the fluid storage accessory comprises a vessel closure.

7. The fluid transport apparatus of claim 1, wherein the fluid storage accessory comprises a vessel.

8. The fluid transport apparatus of claim 7, further comprising a sterilizing vent filter engaged with the vessel configured to allow gaseous transfer therethrough.

9. A flexible conduit for directing fluids therethrough, comprising:
a flexible tube formed of platinum catalyzed silicone rubber having methyl and phenyl side groups and having less than 0.5 weight percent extractables, the flexible tube having a storage modulus of $10^8$ or less Pascals at −75 degrees Celsius.

10. The flexible conduit of claim 9, wherein the platinum catalyzed silicone rubber having methyl and phenyl side groups is substantially free of organic solvent.

11. A storage method, comprising:
providing a biological material;
providing a fluid transport apparatus defining an aseptic pathway configured to direct fluids therethrough, the fluid transport apparatus comprising:
a conduit having a first terminus and a second terminus, the conduit extending between the first terminus and the second terminus, the conduit formed of platinum catalyzed silicone rubber having methyl and phenyl side groups, the conduit having a storage modulus of $10^8$ or less Pascals at −75 degrees Celsius;
at least one fitting connected to the first terminus; and
a vessel engaged with the second terminus;
directing the biological material through the conduit into the vessel;
sealing the vessel at the conduit; and
cryogenically storing the biological material in the vessel.

12. The storage method of claim 11, wherein providing the biological material comprises providing cells.

13. The storage method of claim 11, wherein providing the biological material comprises providing therapeutic proteins.

14. The storage method of claim 11, further comprising engaging a sterilizing vent filter with the vessel to allow gaseous transfer therethrough.

15. The fluid transport apparatus of claim 1, wherein the conduit is an aseptic conduit.

16. The fluid transport apparatus of claim 1, wherein the conduit is configured to transfer pharmaceutical products therethrough.

17. The fluid transport apparatus of claim 1, wherein the conduit is configured to prevent contamination of samples received therein.

18. The fluid transport apparatus of claim 9, wherein the flexible conduit is an aseptic conduit.

19. The fluid transport apparatus of claim 9, wherein the flexible conduit is configured to transfer pharmaceutical products therethrough.

20. The fluid transport apparatus of claim 9, wherein the flexible conduit is configured to prevent contamination of samples received therein.

* * * * *